United States Patent
Crosbie et al.

(10) Patent No.: US 8,134,712 B1
(45) Date of Patent: Mar. 13, 2012

(54) APPARATUS AND METHOD FOR ESTIMATION OF ORE QUALITY USING COLOR CORRELATIONS

(75) Inventors: Mark Crosbie, Hamilton (AU); Colin Howard, Hornsby (AU)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 13/031,286

(22) Filed: Feb. 21, 2011

(51) Int. Cl.
*G01N 21/55* (2006.01)
(52) U.S. Cl. ............. 356/448; 250/269.3; 250/255; 250/359.1; 356/303; 356/219
(58) Field of Classification Search ........... 250/269.3, 250/255, 359.1, 336.1; 356/300–303, 317–319, 356/448
See application file for complete search history.

(56) References Cited

U.S. PATENT DOCUMENTS

| | | | |
|---|---|---|---|
| 3,933,249 A * | 1/1976 | Welsh et al. | 209/557 |
| 7,200,200 B2 * | 4/2007 | Laurila et al. | 250/269.3 |
| 7,835,882 B2 * | 11/2010 | Lambert | 702/137 |

FOREIGN PATENT DOCUMENTS

| | | |
|---|---|---|
| SU | 428255 A1 | 5/1974 |
| SU | 851206 A1 | 8/1981 |
| WO | 2007033415 A1 | 3/2007 |

OTHER PUBLICATIONS

Hayward B. Oblad et al., Control of Fine Coal Flotation Using an Optoelectronic Tailings Ash Detector, Consolidated Coal Co. Research and Development, Proceedings of coalprep 89, 6th international coal preparation exhibition and conference, Lexington, KY, May 2-4,1989.
S. Cierpisz et al., Coal Quality Monitoring and Control in Poland, J. Coal Quality, 13(1), pp. 27-30, Jan.-Mar. 1994.

* cited by examiner

*Primary Examiner* — Gregory J Toatley
*Assistant Examiner* — Iyabo S Alli
(74) *Attorney, Agent, or Firm* — Joshua D. Bishop; Michael B. Martin

(57) ABSTRACT

An apparatus and method for estimating ore quality using color correlations is disclosed. The apparatus and method quantify ash or grade concentration in process streams arid/or samples in real time, allowing for the optimization of ore processing operations, The apparatus and method employ a light beam at a given wavelength, which allows for the measurement of ash content or grade.

12 Claims, 2 Drawing Sheets

APPARATUS AND METHOD FOR ESTIMATION OF ORE QUALITY USING COLOR CORRELATIONS

FIELD OF THE INVENTION

The invention pertains to the estimation of ore quality using a light reflection technique. More particularly, the invention pertains to the estimation of coal fine quality in the tailings stream of a coal processing operation, the quality determined by light reflection at a specific wavelength.

BACKGROUND

Ore processing operations inevitably produce fine particles that in the past led to great process losses. Ore processing operations have developed ways to process these fine particles in order to make the overall operation more efficient than before. To make the fine particle processing as efficient as possible, it is important to know the quality of the fine particles entering the fine particle processing stages of the overall operation. Knowing the quality of the fine particles allows for process adjustments in the fine particle processing stages.

Cierpisz et al., "Coal Quality Monitoring and Control in Poland," discusses the importance of measuring coal quality for such operations. The article initially discusses the measurement of coal quality using a gamma-ray back-scattered method. It continues by discussing the measurement of color in flotation tailings using a MPOF device. The article concludes by discussing various laboratory techniques used to determine the quality of coal.

Oblad et al., "Control of Fine Coal Flotation Using an Optoelectronic Tailings Ash Detector," discusses a new optoelectronic instrument that measures the amount of fine coal in the solids fraction of a slurry of water, coal, and clay, either in the flotation cell or in the tailings. The instrument uses a collimated illumination source and a photoconductor chosen to have the correct voltage or frequency response to measure the internal reflectance of the slurry.

WO/2007/033415, by Lambert, describes a method of online analysis of mineral waste content of a slurry in a mineral separation process, the method including the steps of: measuring the density of the slurry, measuring the concentration of solids in the slurry, calculating the density of solids in the slurry from the slurry density and the solids concentration, and calculating the mineral waste content from the solids density. Lambert also provides an online analyzer for mineral waste content of a slurry in a mineral separation process.

Accordingly, there is a need for estimating the quality of ore in the tailings stream of an ore processing operation. Desirably, the ore quality is determined using a non-destructive, real-time technique. More desirably, once determined, the ore quality can be instantly input into a control loop that controls the coal processing operation, particularly the fine particle processing stages, as efficiently as possible.

SUMMARY OF THE INVENTION

The comparative analysis monitor ("CAM") is a device that allows for quick and simple field tests of ore content in slurry or fine cake. The CAM can be used to provide a measured basis to optimize plant performance. A sample is presented to the CAM, which then produces an output that represents the ash concentration of the sample, a typical measure of ore quality. The sample can be measured continuously, intermittently, or individually. The CAM may be constructed to be easily portable or relatively stationary.

The use of the CAM in process streams allows for dose optimization for frothers, modifiers, promoters, and collectors in flotation circuits and other circuits where addition or subtraction of reagents influences grade, quality, yield, or recovery that can be recognized by color. Additionally, the CAM will allow for detection of fine ore quality in separator process streams including, but not limited to, flotation, spirals, teeter bed separators, reflux classifiers, and shaking tables. The information gathered by the invention can be input into feedback control loops.

The CAM allows for optimization of ore processing operations based on the color of the tailings stream of a separator. The CAM can be used to assess the quality of other materials as well, including but not limited to a feed stream, a concentrate, or a filter cake within an ore processing operation.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE PREFERRED EMBODIMENT

Figure 1:
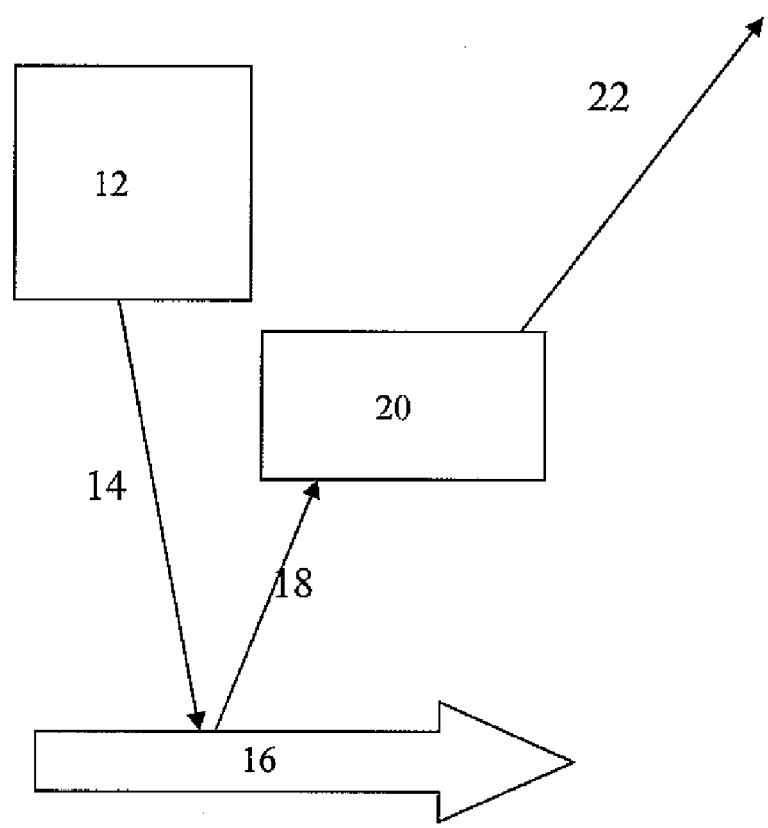
FIG. 1 is a block diagram of the CAM.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Preferred Embodiment," relates to a requirement of the United States Patent Office, and does not imply, nor should be inferred to limit the subject matter disclosed herein.

Figure 2:
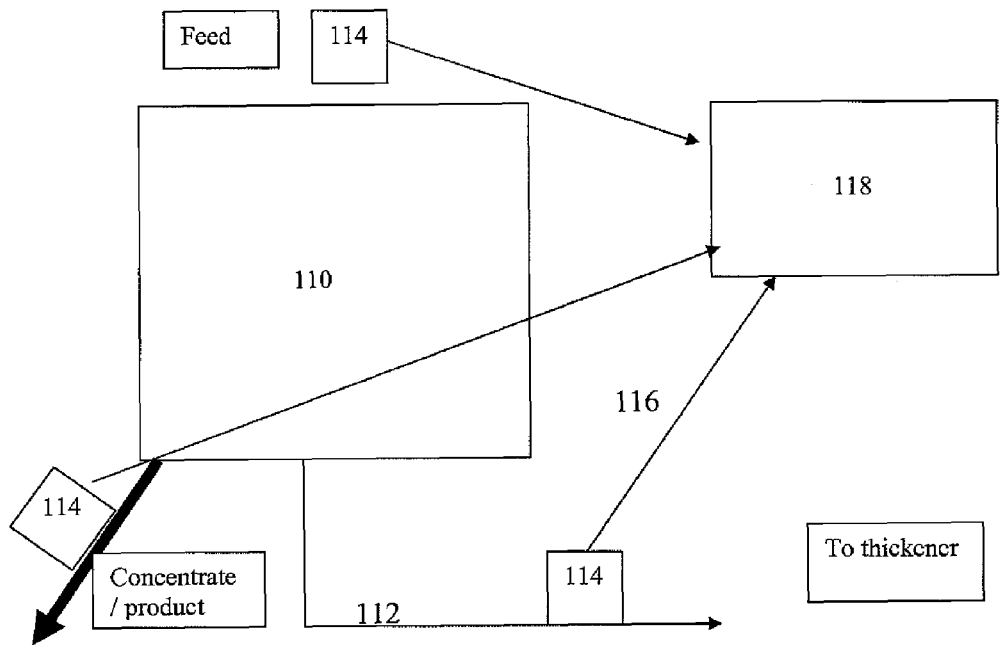
FIG. 2 is a flow diagram of a typical process that includes the installation of a CAM.

As shown in FIG. 1, a light beam generator 12 shines a light beam 14 into a sample 16. The beam 14 has a wavelength in the visible spectrum. Light 18 reflects from the sample 16 and is detected by the detector 20. The detector 20 converts the reflected light 18 into an electrical signal 22, which can be output in several different fashions (not shown). A typical use for the CAM shown in FIG. 2. A flotation separator 110 has a tailings stream 112 that leave the flotation separator 110. The tailings stream 112 can contain fine particles (not shown). The tailings stream 112 is analyzed by the CAM 114, which sends an electrical signal 116 to a control system 118. The electrical signal 116 can vary corresponding to the quality of coal fines that it measures. The tailings stream 112 passes through the CAM 114 and into the thickener. This is intended to illustrate a mere typical use for the CAM and should in no way be construed to limit the invention to this single use.

The control system 118 can be configured to control heating, cooling, pumps, valves, levels, temperature, pressure, or any other process function or parameter, which will be recognized by one skilled in the art.

The CAM 114 can be built to allow for ease of portability, or it can be built to be more or less stationary and devoted to one ore processing operation. The CAM 114 preferably measures the tailings stream 112, but those skilled in the art will recognize that the CAM 114 may be used to measure any of several process streams including, but not limited to, flotation, spirals, teeter bed separators, reflux classifiers, and shaking tables. The CAM 114 may also measure the quality of ore fines in filter cakes.

The CAM 114 preferably outputs an electrical signal having a variable magnitude depending on the measured ore quality. However, those skilled in the art will recognize that the electrical signal can take any of several forms, so long as the signal may vary depending on the measured ore quality.

The CAM 114 may also send the electrical signal to an outputting device, more particularly a visual display (not shown). The visual display can be any of several devices, including, but not limited to, a monitor, a printer, a plotter, a projection screen, and like devices. The outputting device can communicate the ore quality as measured by the CAM 114 as a quantifiable value. The quantifiable value can be a Nalco Slurry Index value.

In an embodiment, the invention is a method for improving ore separation efficiency of an ore processing operation, the method comprising the steps of: analyzing a slurry ash concentration in a process stream of the ore processing operation; outputting an electrical signal corresponding to the slurry ash concentration; wherein the analyzing is performed by shining a light beam into the process stream of the ore processing operation, the light beam having a wavelength in the visible spectrum, and detecting light reflected from the shining of the light beam into a process stream of the ore processing operation. The process stream may be a tailings stream. The ore processing operation may be a coal processing operation.

The method may comprise the additional step of translating the electrical signal into a Nalco Slurry Index value.

The method may comprise the additional step of comparing the Nalco Slurry Index value to a set point, wherein the comparing may provide an input into a control loop controlling the ore processing operation.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

We claim:

1. An apparatus for measuring a quality of ore fines in an ore processing operation, the apparatus comprising:
    a light generator, the light generator generating a focused beam, the focused beam having a wavelength in the visible spectrum;
    a detector, the detector detecting a reflected signal and converting the reflected signal into an electrical signal; and
    an outputting device;
    wherein the light generator shines the focused beam into a process stream of the ore processing operation;
    wherein the detector detects the reflected signal from the light generator shining the focused beam into the process stream of the ore processing operation; and
    wherein the outputting device converts the electrical signal into a quantifiable value corresponding to the quality of ore fines of the process stream of the ore processing operation
    wherein the quality of ore fines corresponds to the slurry ash concentration of the process stream.

2. The apparatus of claim 1, wherein the process stream is a stream to or from a separator.

3. The device of claim 2, wherein the electrical signal is operatively input into a control loop controlling the ore processing operation.

4. The device of claim 2, wherein the electrical signal is a variable signal.

5. The device of claim 2, wherein the outputting device is a visual display.

6. The device of claim 2, wherein the quantifiable value is the Nalco Slurry Index.

7. A method for improving ore separation efficiency of an ore processing operation, the method comprising the steps of:
    analyzing a slurry ash concentration in a process stream of the ore processing operation;
    outputting an electrical signal corresponding to the slurry ash concentration;
    wherein the analyzing is performed by
        shining a light beam into the process stream of the ore processing operation, the light beam having a wavelength in the visible spectrum, and
        detecting light reflected from the shining of the light beam into the process stream of the ore processing operation.

8. The method of claim 7, wherein the process stream is a tailings stream.

9. The method of claim 7, wherein the method comprises the additional step of translating the electrical signal into a Nalco Slurry Index value.

10. The method of claim 9, wherein the method comprises the additional step of comparing the Nalco Slurry Index value to a set point.

11. The method of claim 10, wherein the comparing provides an input into a control loop controlling the ore processing operation.

12. The method of claim 7, wherein the ore processing operation is a coal processing operation.

* * * * *